United States Patent
Haneda et al.

(10) Patent No.: US 10,702,503 B2
(45) Date of Patent: Jul. 7, 2020

(54) CATALASE INHIBITOR AND METHOD FOR MEASURING ANALYTE USING CATALASE INHIBITOR

(71) Applicant: PHC Holdings Corporation, Tokyo (JP)

(72) Inventors: Keigo Haneda, Ehime (JP); Takashi Endoh, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 0 days.

(21) Appl. No.: 16/311,329

(22) PCT Filed: Jun. 20, 2017

(86) PCT No.: PCT/JP2017/022751
§ 371 (c)(1),
(2) Date: Dec. 19, 2018

(87) PCT Pub. No.: WO2017/221944
PCT Pub. Date: Dec. 28, 2017

(65) Prior Publication Data
US 2019/0321335 A1    Oct. 24, 2019

(30) Foreign Application Priority Data
Jun. 21, 2016 (JP) ................................. 2016-122978

(51) Int. Cl.
| | | |
|---|---|---|
| C12Q 1/30 | (2006.01) | |
| A61K 31/4168 | (2006.01) | |
| C12N 9/99 | (2006.01) | |
| G01N 27/416 | (2006.01) | |
| G01N 33/50 | (2006.01) | |
| G01N 33/535 | (2006.01) | |
| C12Q 1/28 | (2006.01) | |
| G01N 21/76 | (2006.01) | |
| G01N 21/78 | (2006.01) | |

(52) U.S. Cl.
CPC ............ *A61K 31/4168* (2013.01); *C12N 9/99* (2013.01); *C12Q 1/28* (2013.01); *C12Q 1/30* (2013.01); *G01N 27/416* (2013.01); *G01N 33/5008* (2013.01); *G01N 33/535* (2013.01); *G01N 21/76* (2013.01); *G01N 21/78* (2013.01); *G01N 2333/908* (2013.01)

(58) Field of Classification Search
CPC ...................................................... C12Q 1/30
See application file for complete search history.

(56) References Cited

FOREIGN PATENT DOCUMENTS

| | | |
|---|---|---|
| EP | 0 409 521 | 1/1991 |
| JP | 63-163164 | 7/1988 |
| JP | 63-254997 | 10/1988 |
| JP | 63-270595 | 11/1988 |
| JP | 2000-236897 | 9/2000 |
| JP | 4462395 | 5/2010 |

OTHER PUBLICATIONS

Chemical Abstracts Registry No. 1205534-16-2, indexed in the Registry file on STN CAS Online Feb. 10, 2010. (Year: 2010).*
International Search Report dated Aug. 8, 2017 in International Application No. PCT/JP2017/022751.
Kitamura, Mitsuru et al., "Direct synthesis of organic azides from primary amines with 2-azido-1, 3-dimethylimidazolinium hexafluorophosphate", Eur. J. Org. Chem., 2011, p. 458-462, DOI: 10.1002./ejoc.201001509.
International Preliminary Report on Patentability dated Jan. 3, 2019 in International (PCT) Application No. PCT/JP2017/022751.
Mitsuru Kitamura et al., "A reagent for safe and efficient diazo-transfer to primary amines: 2-azido-1,3-dimethylimidazolinium hexafluorophosphate", Organic & Biomolecular Chemistry, vol. 12, pp. 4397-4406 (2014).
Bahadur et al., "Synthesis of Diverse Indene Derivatives from 1-Diazonaphthalen-2(1H)-ones via Thermal Cascade Reactions", Organic Letters, vol. 15, No. 17, pp. 4288-4291 (2013).
Extended European Search Report dated Dec. 18, 2019 in corresponding European Patent Application No. 17815412.6.

* cited by examiner

*Primary Examiner* — Joseph R Kosack
(74) *Attorney, Agent, or Firm* — Wenderoth, Lind & Ponack, L.L.P.

(57) ABSTRACT

Provided is a catalase inhibitor comprising a compound represented by formula (I):

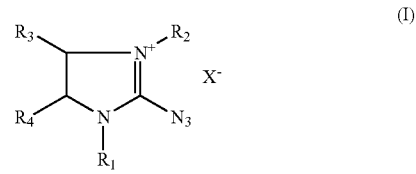

wherein $R_1$ to $R_4$ independently represent a hydrogen atom, a halogen atom, an amino group, a hydroxyl group, a carbonyl group, or a hydrocarbon group having 1 to 4 carbon atoms, wherein the hydrocarbon group may have at least one substituent selected from the group consisting of a halogen atom, an amino group, a hydroxyl group and a carbonyl group; and $X^-$ represents an anionic chemical species.

12 Claims, 4 Drawing Sheets

CATALASE INHIBITOR AND METHOD FOR MEASURING ANALYTE USING CATALASE INHIBITOR

TECHNICAL FIELD

The present application relates to a catalase inhibitor; and a method for measuring an analyte, a measurement kit and the like which use the inhibitor.

BACKGROUND ART

There has been provided a technique in a method for measuring an analyte using an enzyme reaction, where the analyte is measured quantitatively or qualitatively by measuring hydrogen peroxide produced by the reaction of the analyte with a catalyst enzyme. However, because catalase (EC number: 1.11.1.6) decomposes hydrogen peroxide used for measurement of an analyte when blood and the like are used as a sample, a technique where sodium azide is used as a catalase inhibitor has been disclosed (see, for example, Patent Document 1).

Patent Document 1: Japanese Patent No. 4462395

DISCLOSURE OF THE INVENTION

Problems to be Solved by the Invention

Under the above-described situation, a more preferred catalase inhibitor was desired.

Means to Solve the Problems

As a result of intensive studies, the inventors have found that a certain kind of azide compound exhibits a catalase inhibitory action. Accordingly, the present application provides the following aspects:

[1] A catalase inhibitor comprising
a compound represented by formula (I):

[Chem. 1]

(I)

wherein $R_1$ to $R_4$ each independently represents a hydrogen atom, a halogen, an amino group, a hydroxyl group, a carboxyl group, or a hydrocarbon group having 1 to 4 carbons which may contain substituent(s); and $X^-$ represents an anionic chemical species;

[2] The catalase inhibitor according to [1], wherein
$R_1$ to $R_4$ each independently represents a hydrogen atom or a hydrocarbon group having 1 to 4 carbons, wherein the hydrocarbon group may contain at least one kind of substituent selected from the group consisting of a halogen, an amino group, a hydroxyl group, and a carboxyl group; and $X^-$ represents any one selected from the group consisting of a halogen ion, an ion in a compound containing halogen(s), a hydroxide ion, a carboxylate ion, a nitrate ion, a nitrite ion, an acetate ion, a carbonic acid hydrogen ion, a dihydrogen phosphate ion, a hydrogen sulfate ion, a hydrogen sulfide ion, a hydrogen oxalate ion, a cyanate ion, and a thiocyanate ion;

[3] The catalase inhibitor according to [1], wherein
$R_1$ to $R_4$ each independently represents a hydrogen atom or an unsubstituted, straight-chained or branched-chained saturated hydrocarbon group having 1 to 4 carbons; and
$X^-$ represents a halogen ion or an ion in a compound containing halogen(s);

[4] The catalase inhibitor according to [1], wherein
the compound represented by the chemical formula (I) is 2-azido-1,3-dimethylimidazolinium hexafluorophosphate;

[5] A method for measuring an analyte based on production of hydrogen peroxide, comprising the following steps:
(A) a step of mixing a sample and the catalase inhibitor according to any one of [1] to [4], wherein the sample contains the analyte and a catalase;
(B) a step of oxidizing the analyte by a first enzyme to produce hydrogen peroxide; and
(C) a step of measuring the hydrogen peroxide;

[6] The method for measuring an analyte according to [5], wherein
step (B) is performed after step (A) or simultaneously with step (A);

[7] A method for measuring an analyte based on production of a hydrogen peroxide, comprising the following steps:
(a) a step of mixing a sample and the catalase inhibitor according to any one of [1] to [4], wherein the sample contains the analyte and a catalase;
(b-1) a step of producing a substrate from the analyte by a second enzyme;
(b-2) a step of oxidizing the substrate by a first enzyme to produce hydrogen peroxide; and
(c) a step of measuring the hydrogen peroxide;

[8] The method for measuring an analyte according to [7], wherein
the steps are performed:
in an order of (b-1), (a), (b-2), and then (c);
after step (b-1), steps (a) and (b-2) are performed simultaneously, and then step (c) is performed; or
steps (a) and (b-1) are performed simultaneously, and then step (c) is performed after step (b-2);

[9] The method for measuring an analyte according to any one of [5] to [8], wherein
in step (C) or (c), the hydrogen peroxide is measured by a colorimetry, a chemiluminescence method, or an electrochemical method;

[10] A measurement kit which measures an analyte in a sample containing a catalase, comprising:
a first enzyme which catalyzes a reaction where the analyte is oxidized to produce hydrogen peroxide; and
the catalase inhibitor according to any one of [1] to [4];

[11] A measurement kit that measures an analyte in a sample containing a catalase, comprising:
a first enzyme which catalyzes a reaction where a substrate is oxidized to produce hydrogen peroxide;
the catalase inhibitor according to any one of [1] to [4]; and
a second enzyme which catalyzes a reaction where the substrate is produced from the analyte;

[12] The kit according to [10] or [11], further comprising a peroxidase;

[13] A reagent for pretreatment of a sample for measurement by an electrochemical method, comprising
the catalase inhibitor according to any one of [1] to [4];

[14] A kit for pretreatment of a sample for measurement of an analyte in the sample containing a catalase by an electrochemical method, based on production of hydrogen peroxide by oxidization of a substrate by a first enzyme, wherein said kit for pretreatment of the sample comprises:

the catalase inhibitor according to any one of [1] to [4]; and a second enzyme which catalyzes a reaction where the substrate is produced from the analyte;

[15] The measuring method or the kit according to any one of [5] to [12] and [14], wherein the first enzyme is an oxidizing enzyme, and the second enzyme is a degrading enzyme.

Effects of the Invention

The present application provides a more preferred catalase inhibitor and a method for measuring an analyte using the catalase inhibitor.

DESCRIPTION OF PREFERRED EMBODIMENTS

The following describes the embodiments in detail. The embodiments are illustrative and do not limit the invention. All of the features and the combinations thereof described in the embodiments are not necessarily essential for the invention.

1. Catalase Inhibitor of the Present Application

The catalase inhibitor according to a first aspect of the present application (hereinafter also referred to as "catalase inhibitor of the present application") comprises a compound (hereinafter also referred to as a compound (I)) represented by formula (I):

[Chem. 2]

(I)

wherein $R_1$ to $R_4$ each independently represents a hydrogen atom, a halogen, an amino group, a hydroxyl group, a carboxyl group, or a hydrocarbon group having 1 to 4 carbons which may contain a substituent; and $X^-$ represents an anionic chemical species.

The halogen includes bromo, chloro, iodine, or fluoro.

The hydrocarbon group having 1 to 4 carbons includes a straight-chained, branched-chained, or cyclic saturated or unsaturated hydrocarbon group having 1 to 4 carbons. The hydrocarbon group having 1 to 4 carbons may include substituent(s). Examples of this substituent include at least one kind of substituent selected from the group consisting of a halogen, an amino group, a hydroxyl group, and a carboxyl group.

Examples of the anionic chemical species include a halogen ion, an ion in a compound containing halogen(s), a hydroxide ion, a carboxylate ion, a nitrate ion, a nitrite ion, an acetate ion, a carbonic acid hydrogen ion, a dihydrogen phosphate ion, a hydrogen sulfate ion, a hydrogen sulfide ion, a hydrogen oxalate ion, a cyanate ion, or a thiocyanate ion. The anionic chemical species is preferably a halogen ion or an ion in a compound containing halogen(s). The example of the ion in a compound containing halogen(s) includes a hexafluorophosphate ion or a perchlorate ion.

In one specific example, the compound (I) is a compound, wherein $R_1$ and $R_2$ each independently represents a hydrogen atom, an amino group, a hydroxyl group, a carboxyl group, or a hydrocarbon group having 1 to 4 carbons that may contain substituent(s); $R_3$ and $R_4$ each independently represents a hydrogen atom, a halogen, an amino group, a hydroxyl group, a carboxyl group, or a hydrocarbon group having 1 to 4 carbons that may contain substituent(s); the hydrocarbon group may contain at least one kind of substituent selected from the group consisting of a halogen, an amino group, a hydroxyl group, and a carboxyl group; and $X^-$ represents any one selected from the group consisting of a halogen ion, an ion in a compound containing halogen(s), a hydroxide ion, a carboxylate ion, a nitrate ion, a nitrite ion, an acetate ion, a carbonic acid hydrogen ion, a dihydrogen phosphate ion, a hydrogen sulfate ion, a hydrogen sulfide ion, a hydrogen oxalate ion, a cyanate ion, and a thiocyanate ion.

In another specific example, the compound (I) is a compound, wherein $R_1$ to $R_4$ each independently represents a hydrogen atom or a straight-chained, branched-chained, or cyclic saturated or unsaturated hydrocarbon group having 1 to 4 carbons, wherein the hydrocarbon group may contain at least one kind of substituent selected from the group consisting of the a halogen, an amino group, a hydroxyl group, and a carboxyl group; and $X^-$ represents any one selected from the group consisting of a halogen ion, an ion in a compound containing halogen(s), a hydroxide ion, a carboxylate ion, a nitrate ion, a nitrite ion, an acetate ion, a carbonic acid hydrogen ion, a dihydrogen phosphate ion, a hydrogen sulfate ion, a hydrogen sulfide ion, a hydrogen oxalate ion, a cyanate ion, and a thiocyanate ion.

In yet another specific example, the compound (I) is a compound, wherein $R_1$ to $R_4$ each independently represents a hydrogen atom or a straight-chained or branched-chained saturated or unsaturated hydrocarbon group having 1 to 4 carbons, wherein the hydrocarbon group may contain at least one kind of substituent selected from the group consisting of a halogen, an amino group, a hydroxyl group, and a carboxyl group; and $X^-$ represents any one selected from the group consisting of a halogen ion, an ion in a compound containing halogen(s), a hydroxide ion, a carboxylate ion, a nitrate ion, a nitrite ion, an acetate ion, a carbonic acid hydrogen ion, a dihydrogen phosphate ion, a hydrogen sulfate ion, a hydrogen sulfide ion, a hydrogen oxalate ion, a cyanate ion, and a thiocyanate ion.

In yet another specific example, the compound (I) is a compound, wherein $R_1$ to $R_4$ each independently represents a hydrogen atom or an unsubstituted, straight-chained or branched-chained saturated or unsaturated hydrocarbon group having 1 to 4 carbons; and $X^-$ represents a halogen ion or an ion in a compound containing halogen(s).

In yet another specific example, the compound (I) is a compound represented by the following structural formula:

[Chemical Formula 3]

namely, 2-azido-1,3-dimethylimidazolinium hexafluorophosphate.

The catalase inhibitor of the present application may be the compound (I) itself. Alternatively, in addition to the compound (I), an additional constituent not affecting a catalase inhibitory action of the compound (I) such as water, solvent, buffer solution, protein, a high-polymer material, saccharide, salts, surfactant, oxidant, and reductant may be contained in the catalase inhibitor as necessary.

2. Measuring Method of the Present Application

The catalase inhibitor of the present application can be used for, for example, a method for measuring an analyte based on production of hydrogen peroxide. Accordingly, as a second aspect of the present invention, the method for measuring an analyte based on the production of hydrogen peroxide using the catalase inhibitor of the present application (hereinafter also referred to as "measuring method of the present application") is provided.

In the description of the present application, "analyte" means a measurement-target substance.

In the description of the present application, "measurement" includes both "quantitative" and "qualitative" measurements.

In the measuring method of the present application, a substrate contained in a sample is oxidized by a first enzyme and hydrogen peroxide produced by the oxidation reaction is measures to measure the analyte. The oxidation reaction is carried out under the presence of the catalase inhibitor of the present application. The substrate may be the analyte itself or may be produced from the analyte through one or more enzyme reactions (reactions by a second enzyme). In the measuring method of the present application, the amount of produced hydrogen peroxide is proportionate to the amount of analyte contained in a sample. Accordingly, the amount of analyte contained in the sample can be calculated using a preliminarily created calibration curve based on the amount of hydrogen peroxide.

The first enzyme is an enzyme which catalyzes a reaction where a substrate is oxidized to produce hydrogen peroxide. The first enzyme can be appropriately determined according to the kind of analyte to be measured. The example of the first enzyme includes oxidizing enzyme (oxidase). Although not limited, examples of the oxidizing enzyme include glucose oxidase (EC number: 1.1.3.4), hexose oxidase (EC number: 1.1.3.5), cholesterol oxidase (EC number: 1.1.3.6), aryl-alcohol oxidase (EC number: 1.1.3.7), L-gulonolactone oxidase (EC number: 1.1.3.8), galactose oxidase (EC number: 1.1.3.9), pyranose oxidase (EC number: 1.1.3.10), L-sorbose oxidase (EC number: 1.1.3.11), pyridoxine 4-oxidase (EC number), alcohol oxidase (EC number: 1.1.3.13), (S)-2-hydroxy-acid oxidase (EC number: 1.1.3.15), ecdysone oxidase (EC number: 1.1.3.16), choline oxidase (EC number: 1.1.3.17), secondary-alcohol oxidase (EC number: 1.1.3.18), 4-hydroxymandelate oxidase (EC number: 1.1.3.19), long-chain-alcohol oxidase (EC number: 1.1.3.20), glycerol-3-phosphate oxidase (EC number: 1.1.3.21), thiamine oxidase (EC number: 1.1.3.23), hydroxyphytanate oxidase (EC number: 1.1.3.27), N-acylhexosamine oxidase (EC number: 1.1.3.29), polyvinyl-alcohol oxidase (EC number: 1.1.3.30), D-arabinono-1,4-lactone oxidase (EC number: 1.1.3.37), vanillyl-alcohol oxidase (EC number: 1.1.3.38), nucleoside oxidase (EC number: 1.1.3.39), D-mannitol oxidase (EC number: 1.1.3.40), alditol oxidase (EC number: 1.1.3.41), prosolanapyrone-II oxidase (EC number: 1.1.3.42), paromamine 6'-oxidase (EC number: 1.1.3.43), 6'''-hydroxyneomycin C oxidase (EC number: 1.1.3.44), aclacinomycin-N oxidase (EC number: 1.1.3.45), 4-hydroxymandelate oxidase (EC number: 1.1.3.46), 5-(hydroxymethyl)furfural oxidase (EC number: 1.1.3.47), aldehyde oxidase (EC number: 1.2.3.1), pyruvate oxidase (EC number: 1.2.3.3), oxalate oxidase (EC number: 1.2.3.4), glyoxylate oxidase (EC number: 1.2.3.5), pyruvate oxidase (CoA-acetylating) (EC number: 1.2.3.6), indole-3-acetaldehyde oxidase (EC number: 1.2.3.7), pyridoxal oxidase (EC number: 1.2.3.8), aryl-aldehyde oxidase (EC number: 1.2.3.9), abscisic-aldehyde oxidase (EC number: 1.2.3.14), protoporphyrinogen oxidase (EC number: 1.3.3.4), acyl-CoA oxidase (EC number: 1.3.3.6), dihydrouracil oxidase (EC number: 1.3.3.7), tetrahydroberberine oxidase (EC number: 1.3.3.8), tryptophan alpha,beta-oxidase (EC number: 1.3.3.10), L-galactonolactone oxidase (EC number: 1.3.3.12), albonoursin synthase (EC number: 1.3.3.13), aclacinomycin-A oxidase (EC number: 1.3.3.14), D-aspartate oxidase (EC number: 1.4.3.1), L-amino-acid oxidase (EC number: 1.4.3.2), D-amino-acid oxidase (EC number: 1.4.3.3), monoamine oxidase (EC number: 1.4.3.4), pyridoxal 5'-phosphate synthase (EC number: 1.4.3.5), D-glutamate oxidase (EC number: 1.4.3.7), ethanolamine oxidase (EC number: 1.4.3.8), putrescine oxidase (EC number: 1.4.3.10), L-glutamate oxidase (EC number: 1.4.3.11), cyclohexylamine oxidase (EC number: 1.4.3.12), protein-lysine 6-oxidase (EC number: 1.4.3.13), L-lysine oxidase (EC number: 1.4.3.14), D-glutamate(D-aspartate) oxidase (EC number: 1.4.3.15), L-aspartate oxidase (EC number: 1.4.3.16), glycine oxidase (EC number: 1.4.3.19), L-lysine 6-oxidase (EC number: 1.4.3.20), primary-amine oxidase (EC number: 1.4.3.21), diamine oxidase (EC number: 1.4.3.22), 7-chloro-L-tryptophan oxidase (EC number: 1.4.3.23), sarcosine oxidase (EC number: 1.5.3.1), N-methyl-L-amino-acid oxidase (EC number: 1.5.3.2), (S)-6-hydroxynicotine oxidase (EC number: 1.5.3.5), (R)-6-hydroxynicotine oxidase (EC number: 1.5.3.6), L-pipecolate oxidase (EC number: 1.5.3.7), dimethylglycine oxidase (EC number: 1.5.3.10), dihydrobenzophenanthridine oxidase (EC number: 1.5.3.12), N(1)-acetylpolyamine oxidase (EC number: 1.5.3.13), polyamine oxidase (propane-1,3-diamine-forming) (EC number: 1.5.3.14), N(8)-acetylspermidine oxidase (propane-1,3-diamine-forming) (EC number: 1.5.3.15), spermine oxidase (EC number: 1.5.3.16), non-specific polyamine oxidase (EC number: 1.5.3.17), L-saccharopine oxidase (EC number: 1.5.3.18), 4-methylaminobutanoate oxidase (formaldehyde-forming) (EC number: 1.5.3.19), N-alkylglycine oxidase (EC number: 1.5.3.20), 4-methylaminobutanoate oxidase (methylamine-forming) (EC number: 1.5.3.21), fructosyl amino-acid oxidase (EC number: 1.5.3), fructosyl peptide oxidase (EC number: 1.5.3), NAD(P)H oxidase ($H_2O_2$-forming) (EC number: 1.6.3.1), NAD(P)H oxidase ($H_2O$-forming) (EC number: 1.6.3.2), (NADH oxidase ($H_2O_2$-forming) (EC number: 1.6.3.3), NADH oxidase $H_2O$-forming (EC number: 1.6.3.4), nitroalkane oxidase (EC number: 1.7.3.1), uric acid oxidase (EC number: 1.7.3.3), 3-aci-nitropropanoate oxidase (EC number: 1.7.3.5), sulfite oxidase (EC number: 1.8.3.1), thiol oxidase (EC number: 1.8.3.2), glutathione oxidase (EC number: 1.8.3.3), methanethiol oxidase (EC number: 1.8.3.4), prenylcysteine oxidase (EC number: 1.8.3.5), farnesylcysteine lyase (EC number: 1.8.3.6), 3-hydroxyanthranilate oxidase (EC number: 1.10.3.5), xanthine oxidase (EC number: 1.17.3.2), 6-hydroxynicotinate dehydrogenaze (EC number: 1.17.3.3), and reticuline oxidase (EC number: 1.21.3.3).

Although not limited, examples of the substrate of the first enzyme include glucose, hexose, cholesterol, aromatic primary alcohol, primary alcohol, L-gulonolactone, galactose, pyranose, L-sorbose, pyridoxine, hydroxy acid, ecdysone, choline, secondary alcohol, 4-hydroxymandelic acid, glycerol-3-phosphate, thiamine, hydroxyphytanate, N-acetyl glucosamine, polyvinyl alcohol, D-arabinono-1,4-lactone, vanillyl alcohol, nucleoside, D-mannitol, alditol, prosolanapyrone II, paromamine, 6-hydroxyneomycin C, aclacinomycin-N, 4-hydroxymandelic acid, 5-hydroxymethylfurfural, aldehyde, pyruvic acid, oxalic acid, glyoxylic acid, pyridoxal, aromatic aldehyde, abscisic aldehyde, protoporphyrinogen, acyl-CoA, dihydrouracil, tetrahydroberberine, tryptophan, L-galactonolactone, aclacinomycin-A, D-aspartic acid, L-amino acid, D-amino acid, monoamine, pyridoxamine-5'-phosphate, D-glutamic acid, ethanolamine, putrescine, L-glutamic acid, cyclohexylamine, peptidyl-L-lysyl-peptide, L-lysine, L-aspartic acid, glycine, primary amine, diamine, 7-chloro-L-tryptophan, sarcosine, N-methyl-L-amino-acid, hydroxynicotine, L-pipecolic acid, dimethylglycine, dihydrosanguinarine, dihydrochelirubine, dihydromacarpine, N1-acetylspermidine, N1-acetylspermine, spermidine, N8-acetylspermidine, spermine, L-saccharopine, 4-methylaminobutanoate, N-alkylglycine, fructosyl amino-acid, fructosyl peptide, NAD(P)H, NADH, nitroalkane, uric acid, 3-aci-nitropropanoic acid, sulfurous acid, thiol, glutathione, methanethiol, prenylcysteine, farnesylcysteine, 3-hydroxyanthranilic acid, xanthine, 6-hydroxynicotinic acid, and reticuline.

The sample contains an analyte and contains a catalase or possibly contains catalase. In the description of the present application, the sample is referred to as "sample containing the analyte and a catalase." Although not limited, the examples of the samples include blood samples (for example, a diluted blood sample derived from a human) such as the whole blood, a blood plasma, a serum, a blood cell, and a blood dilution; a biological sample such as urine, spinal fluid, sweat, tear fluid, saliva, skin, mucous membrane, and hair; and a beverage such as various food products or their extracts, alcohol, and soft drink. The biological samples are not limited to the samples derived from the human. The blood sample on which a hemolysis treatment has been performed is preferably used. The hemolysis treatment may be performed by conventional method.

Since catalase decomposes hydrogen peroxide, the presence of catalase in the sample deteriorates measurement accuracy in the method for measuring an analyte based on the production of hydrogen peroxide like the present application. That is, since hydrogen peroxide produced by the reaction by the first enzyme is consumed by catalase, the influence from the catalase results in a failure of the measurement of the accurate amount of hydrogen peroxide produced depending on the amount of analyte when the amount of produced hydrogen peroxide is attempted to be measured. Therefore, in the measuring method of the present application, the reaction by the first enzyme is carried out under the presence of the catalase inhibitor. For example, before or simultaneous with processing the sample with the first enzyme, the sample and the catalase inhibitor are mixed. The catalase inhibitor used here is the catalase inhibitor of the present application.

In the prior art, the influence from the catalase has been suppressed by coexistence of sodium azide in a reaction chamber. However, as a result of intensive examinations of the technique to measure the hydrogen peroxide produced by the reaction by the oxidizing enzyme, the inventors have found that the sodium azide is not preferred for a system using an electrochemical method. Specifically, the inventors have found that although the sodium azide has an inhibitory activity of catalase, the sodium azide causes the deterioration of measurement accuracy in the analyte measurement by the electrochemical method. The less the amount of measured analyte was, the more the influence on the deterioration of measurement accuracy caused by the sodium azide became remarkable. It was possibly thought that azide ions released from the sodium azide in the solution adsorb to an electrode and a catalytic activity of the electrode is lowered and a redox reaction of the hydrogen peroxide is suppressed.

On the other hand, since an azido group is covalently bonded in the compound (I) contained in the catalase inhibitor of the present application, the azide ions are not rapidly released in the solution. Therefore, it is inferred that the influence from the compound (I) to the catalytic activity of the electrode is more moderate compared with that of the sodium azide. Actually, as described in working examples, in case that the catalase inhibitor of the present application was used, the deterioration of measurement accuracy like when the sodium azide was used was not observed. It is obvious that the catalase inhibitor of the present application can be used not only for a technique to measure the hydrogen peroxide by electrochemical method but also for a technique to measure the hydrogen peroxide by other methods such as colorimetry and a chemiluminescence method.

In the measuring method of the present application, the amount of catalase inhibitor of the present application mixed with the sample is not specifically limited and appropriately determined according to the measured sample and the measuring conditions. Although not limited, a final concentration at reaction of the compound (I) is, for example, in a range of about 175 μM to about 4.5 mM, about 200 μM to about 4 mM, about 250 μM to about 4 mM, about 300 μM to about 3.5 mM, or about 350 μM to about 3.5 mM.

In the measuring method of the present application, hydrogen peroxide may be measured by any method known in the art. Although not limited, for example, the colorimetry, the chemiluminescence method, or the electrochemical method is employable.

In the example of the measuring method by colorimetry, the hydrogen peroxide produced in association with the oxidization of the substrate by the first enzyme is reacted with a coloring reagent under the presence of peroxidase (EC number: 1.11.1.7). The coloring reagent is a substance from which hydrogen is removed by a reaction with the hydrogen peroxide promoted by the peroxidase to develop a color. Although not limited, the examples of the coloring reagent are well known in the art and include N-(carboxymethylaminocarbonyl)-4,4'-bis(dimethylamino)diphenylamine sodium salt, 10-(carboxymethylaminocarbonyl)-3,7-bis(dimethylamino)phenothiazine sodium salt, 3,3',5,5'-tetramethylbenzidine, 3,3-diamino benzidine, N,N-bis(2-hydroxy-3-sulfopropyl)tolidine, 2,2'-azinobis(3-ethylbenzothiazoline-6-sulfonic acid ammonium salt), orthophenylenediamine, and a combination of a phenolic compound or an aniline derivative and 4-aminoantipyrine or 3-methyl-2-benzothiazolinone hydrazone. The reaction with the coloring reagent can produce a pigment according to the amount of hydrogen peroxide. Accordingly, the amount of hydrogen peroxide can be quantified by detecting a pigment produced using the measurement of absorbance in a wavelength corresponding to the coloring reagent. And, since the amount of hydrogen peroxide correlates to the amount of analyte, the analyte can be quantified by measuring the amount of hydrogen peroxide. In the measuring method of this type, generally the oxidation reaction by a first enzyme and the reaction by a peroxidase are carried out in the identical reaction chamber.

In the example of the measuring method by chemiluminescence, hydrogen peroxide produced in association with the oxidization of the substrate by the first enzyme is reacted with a luminescence reagent under the presence of peroxidase (EC number: 1.11.1.7). The luminescence reagent is a substance from which hydrogen is removed by a reaction with hydrogen peroxide promoted by peroxidase to emit light. Although not limited, the examples of the luminescence reagent are well known in the art and include luminol, isoluminol, N-(4-aminobutyl)-N-ethylisoluminol, lucigenin, and acridinium ester. An amount of light according to the amount of hydrogen peroxide can be produced by the reaction with the luminescence reagent. Therefore, the amount of hydrogen peroxide can be quantified by determining the amount of the light of the luminescence reagent. Since the amount of hydrogen peroxide correlates to the amount of analyte, the analyte can be quantified by measuring the amount of hydrogen peroxide. In the measuring method of this type, generally the oxidation reaction by the first enzyme and the reaction by peroxidase are carried out in the same reaction chamber.

In the example of the measuring method by electrochemical method, a current value according to the amount of hydrogen peroxide is detected by application of a predetermined voltage to the hydrogen peroxide produced in association with the oxidization of the substrate by the first enzyme. Accordingly, the amount of hydrogen peroxide can be quantified by detecting this current value. Since the amount of hydrogen peroxide correlates to the amount of the analyte, the analyte can be quantified by measuring the amount of hydrogen peroxide. Here, "predetermined voltage" means an electric potential where the hydrogen peroxide is oxidized or reduced. The person skilled in the art can appropriately set the predetermined voltage depending on various conditions such as an electrode material and pH. For example, in case of a three-electrode system (a working electrode (for example, platinum or palladium), a counter electrode, and a reference electrode (for example, silver/silver chloride (saturated potassium chloride) electrode)), although different depending on the electrode material, pH, and the like, applying a voltage around 0.6 V oxidizes the hydrogen peroxide in most cases. In case of a two-electrode system (the working electrode and the counter electrode), although substantially different depending on the conditions and case-by-case, the example of the method includes an application of a voltage around 0.2 V to 0.5 V to oxidize the hydrogen peroxide.

In the electrochemical method, for example, an electrode pair including a working electrode and a counter electrode, or three electrodes including a working electrode, a counter electrode and a reference electrode are used. A predetermined voltage is applied between the working electrode and the counter electrode, or a predetermined voltage for the reference electrode is applied to a working electrode, and the redox reaction of hydrogen peroxide is occurred to measure the current value flowing through the working electrode or an amount of electric charge. For example, a first enzyme may be supported on an electrode. When a first enzyme is supported on an electrode, mixed liquid of a sample and the catalase inhibitor of the present application are spotted on the electrode, or the electrode is immersed in the mixed liquid to produce hydrogen peroxide on the electrode. Alternatively, a first enzyme and the catalase inhibitor of the present application may be supported to the electrode, and a sample may be spotted on the electrode, or the electrode may be immersed in a sample. The electrochemical method to determine the quantity of the hydrogen peroxide and the electrodes used for the method are well-known in the art. The method to make the enzyme and the inhibitor to be supported on an electrode may also be any method which can make the desired enzyme or inhibitor to be supported on an electrode, and said method is not specifically limited. Any method known in the art can be used. For example, an inkjet method may be used.

The following describes specific examples of the measuring method of the present application.

One example of the measuring method of the present application is the method for measuring an analyte based on production of hydrogen peroxide. The measuring method comprises:

(A) a step of mixing a sample and a catalase inhibitor containing a compound (I), wherein the sample containing the analyte and a catalase;

(B) a step of oxidizing the analyte by a first enzyme to produce hydrogen peroxide; and (C) a step of measuring the hydrogen peroxide. In this measuring method, the analyte is a substrate of the first enzyme.

In step (B), the first enzyme and the sample are mixed, and the analyte is oxidized to produce hydrogen peroxide. Here, the oxidation reaction conditions are not specifically limited, and the person skilled in the art can appropriately determine the conditions. Step (B) is performed after step (A) or performed simultaneously with step (A).

In step (C), the hydrogen peroxide produced in step (B) is measured. For example, an amount of the hydrogen peroxide produced in step (B) is measured.

Step (C) may be performed after steps (A) and (B), or may be performed simultaneously with step (B). For example, the steps may be performed in the order of steps (A) and (B) and then (C), or steps (A) and (B) may be performed simultaneously and then step (C) may be performed. Alternatively, after step (A), steps (B) and (C) may be performed simultaneously, or all steps (A) to (C) may be performed simultaneously. An example of simultaneously performing steps (B) and (C) after step (A) includes the case where the sample and the catalase inhibitor of the present application are mixed, and then the mixed liquid is introduced in a reaction chamber containing the first enzyme and a reagent to measure the hydrogen peroxide (for example, peroxidase, coloring reagent, or luminescence reagent), or the case where the mixed liquid is added on an electrode supporting the first enzyme on which a voltage has been applied. An example of simultaneously performing all steps (A) to (C) includes the case where the sample, the catalase inhibitor of the present application, the first enzyme, and a reagent to measure hydrogen peroxide (for example, the peroxidase, the coloring reagent, or the luminescence reagent) is simultaneously introduced in the same reaction chamber, or the case where the sample is added on an electrode supporting the catalase inhibitor of the present application and the first enzyme on which the voltage has been applied.

The above examples describe the system for measurement which includes step (B) to produce hydrogen peroxide in association with oxidization of the analyte by the first enzyme, and step (C) to measure the produced hydrogen peroxide. However, the measuring method of the present application is not limited to this system for measurement, and also includes a method for measuring an analyte through multiple enzyme reactions. An example of the measuring method of the present application through the multiple enzyme reactions includes a system for measurement which comprises a step of reacting an analyte with a second enzyme to obtain a product (substrate), a step of oxidizing this product (substrate) by the above-described first enzyme (for example, the oxidizing enzyme) to produce hydrogen peroxide, and a step of measuring the produced hydrogen peroxide.

Accordingly, yet another example of the measuring method of the present application is a method for measuring an analyte based on production of hydrogen peroxide. The measuring method comprises:
(a) a step of mixing a sample and a catalase inhibitor containing a compound (I), wherein the sample containing the analyte and a catalase;
(b-1) a step of producing a substrate from the analyte by a second enzyme;
(b-2) a step of oxidizing the substrate by a first enzyme to produce hydrogen peroxide; and
(c) a step of measuring the hydrogen peroxide.

In the measuring method, the analyte is a substance which produces the substrate of the first enzyme by catalytic action of the second enzyme. Although not limited, the examples of the analyte include a protein, for example, glycated hemoglobin [for example, hemoglobin A1c (hereinafter abbreviated as "HbA1c")] and glycated albumin.

In step (b-1), the second enzyme and the sample are mixed to produce the substrate of the first enzyme from the analyte contained in the sample. The second enzyme is not specifically limited and can be appropriately determined depending on the kind of analyte. The example of the second enzyme includes a degrading enzyme (such as protease and peptidase). The conditions of the reaction by the second enzyme are not specifically limited, and the person skilled in the art can appropriately determine the conditions. For example, the reaction may be carried out under coexistence of a substance promoting the production of the substrate from the analyte.

The reaction which produces the substrate of the first enzyme from the analyte in step (b-1) may be one-step reaction or may be a multiple-step reaction. When the substrate of the first enzyme is produced from the analyte by multiple-step reaction, the second enzyme contains a plurality of enzymes.

In step (b-2), the first enzyme and the sample are mixed, and the substrate contained in the sample is oxidized to produce the hydrogen peroxide. The substrate is produced in step (b-1). Here, the oxidation reaction conditions are not specifically limited, and the person skilled in the art can appropriately determine conditions of the oxidation reaction.

In step (c), the hydrogen peroxide produced in step (b-2) is measured. For example, the amount of the hydrogen peroxide produced in step (b-2) is measured.

Step (b-1) may be performed before step (a), or may be performed simultaneously with step (a). Alternatively, step (b-1) is performed before step (b-2), or performed simultaneously with step (b-2). Step (b-2) is performed after step (a), or performed simultaneously with step (a). For example, the steps may be performed in the order of steps (a), (b-1), and (b-2), and then (c), or may be performed in the order of steps (b-1), (a), (b-2), and then (c), or after step (a), steps (b-1) and (b-2) may be performed simultaneously and then step (c) may be performed, or after step (a), steps (b-1), (b-2), and (c) may be performed simultaneously, or after step (b-1), steps (a) and (b-2) may be performed simultaneously and then step (c) may be performed, or after step (b-1), steps (a), (b-2), and (c) may be performed simultaneously, or steps (a) and (b-1) may be performed simultaneously, and after step (b-2), step (c) may be performed, or steps (a) and (b-1) may be performed simultaneously and then steps (b-2) and (c) may be performed simultaneously, or steps (a), (b-1), and (b-2) may be performed simultaneously, and then step (c) may be performed, or all steps (a) to (c) may be performed simultaneously. The example of simultaneously performing all steps (a) to (c) includes the case where the sample, the catalase inhibitor of the present application, the first enzyme, the second enzyme, and the reagent to measure the hydrogen peroxide (for example, the peroxidase, the coloring reagent, or the luminescence reagent) are simultaneously introduced in the same reaction chamber, or the case where the sample is added on an electrode supporting the catalase inhibitor of the present application, the first enzyme, and the second enzyme, on which the voltage has been applied.

The following specifically describes a measurement using HbA1c as the analyte, as one example of the measuring method of the present application through the multiple enzyme reactions as described above. In the measurement of HbA1c, for example, a blood sample or a blood cell sample is used as a sample. The sample and the catalase inhibitor of the present application are mixed in step (a). In step (b-1), a protease as the second enzyme is used to produce fructosyl-valyl-histidine (Fru-Val-His) as glycated peptide from HbA1c in the sample. Next, in step (b-2), the glycated peptide produced at step (b-1) is oxidized with a fructosyl peptide oxidase (FPOX) as the first enzyme to produce the hydrogen peroxide. Next, in step (c), the hydrogen peroxide produced in step (b-2) is measured. Examples of the protease include metalloprotease (for example, thermolysin), cysteine protease (for example, papain and caspase), and serine protease (for example, chymotrypsin and subtilisin). Furthermore, step (b-1) may be performed under the presence of a substance which promotes the decomposition of the analyte with the protease. Examples of such substance include surfactant, such as nonionic surfactant, anionic surfactant, and cationic surfactant; and a tetrazolium compound. The protease which produces fructosyl-valine (Fru-Val) as glycated amino acid from HbA1c may be used as the second enzyme in step (b-1), and fructosyl amino-acid oxidase (FAOX) may be used instead of the fructosyl peptide oxidase as the first enzyme in step (b-2).

Since the catalase inhibitor comprising the compound (I) and the sample are mixed in the measuring method of the present application, the amount of hydrogen peroxide produced by the oxidization of the analyte or the amount of hydrogen peroxide produced by the oxidization of the substrate produced from the analyte can be accurately measured by the use of any method of the colorimetry, the chemiluminescence method, or the electrochemical method for measurement of the hydrogen peroxide.

3. Measurement Kit for the Present Application

Next, the following describes the measurement kit (hereinafter also referred to as "measurement kit of the present application") according to a third aspect of the present application which measures an analyte in a sample containing a catalase.

The measurement kit of the present application is that to measure an analyte in a sample containing a catalase, and is used to measure the analyte based on the production of hydrogen peroxide. In the description of the present application, "a sample containing a catalase" includes a sample containing a catalase and a sample possibly containing a catalase.

A first example of the measurement kit of the present application comprises a first enzyme which catalyzes a reaction where an analyte is oxidized to produce hydrogen peroxide, and the catalase inhibitor of the present application. A second example of the measurement kit of the present application comprises a first enzyme which catalyzes a reaction where a substrate is oxidized to produce hydrogen peroxide, the catalase inhibitor of the present application, and a second enzyme which catalyzes a reaction where the substrate of the first enzyme is produced from the analyte. In the first example of the measurement kit of the present application, the analyte is the substrate of the first enzyme. In the second example of the measurement kit of the present application, the analyte is a substance which produces the substrate of the first enzyme. The examples of the first enzyme and the second enzyme are as described above.

The measurement kit of the present application may further include a peroxidase. The measurement kit of the present application comprising the peroxidase is used to measure the analyte through the measurement of the hydrogen peroxide by, for example, colorimetry or chemiluminescence method.

4. Reagent for Pretreatment of Sample of the Present Application

Next, the following describes a reagent for pretreatment of sample (hereinafter also referred to as "reagent for pretreatment of a sample of the present application") according to a fourth aspect of the present application, which comprises the compound (I) for measurement by electrochemical method.

The reagent for pretreatment of a sample of the present application is used to process the sample before the measurement whent the analyte in the sample containing the catalase is measured by electrochemical method. For example, the reagent for pretreatment of a sample of the present application is used to pretreat the sample which is submitted to a method for measuring the analyte based on the production of the hydrogen peroxide where hydrogen peroxide is measured by electrochemical method. In this case, the oxidization of the analyte catalyzed by the first enzyme produces hydrogen peroxide, and this first enzyme is supported on the electrode. The reagent for pretreatment of a sample of the present application may comprise an additional constituent which does not affect the catalase inhibitory action of the compound (I), such as water, solvent, buffer solution, protein, a high-polymer material, saccharide, salts, surfactant, oxidant, and reductant, as necessary.

5. Kit for Pretreatment of Sample of the Present Application

Next, the following describes the kit for pretreatment of a sample (hereinafter also referred to as "kit for pretreatment of a sample of the present application") according to a fifth aspect of the present application for measurement of the analyte in the sample containing catalase by electrochemical method.

A kit comprising the catalase inhibitor of the present application and a second enzyme is provided as the kit for pretreatment of sample of the present application. The second enzyme is an enzyme that catalyzes a reaction producing the substrate of the first enzyme from the analyte in the sample. The examples of the first enzyme and the second enzyme are as described above.

The kit for pretreatment of sample of the present application is used to process the sample before the measurement when the analyte in the sample containing the catalase is measured by electrochemical method. For example, the kit for pretreatment of a sample of the present application is used to pretreat the sample which is submitted to a method for measurement of an analyte based on production of hydrogen peroxide, where the hydrogen peroxide is produced by the oxidation of the substrate produced from the analyte, and the hydrogen peroxide is measured by an electrochemical method. In this case, the first enzyme is supported on an electrode used in the electrochemical method.

Furthermore, a kit comprising a first enzyme, the catalase inhibitor of the present application, and a second enzyme is provided as the kit for pretreatment of a sample of the present application. The first enzyme and the second enzyme are as described above. This kit can be used when the first enzyme is not supported on an electrode used in an electrochemical method.

Furthermore, as the kit for pretreatment of a sample of the present application, a kit comprising a first enzyme and the catalase inhibitor of the present application is provided. The first enzyme is as described above. This kit can be used when hydrogen peroxide is produced by oxidation of the analyte catalyzed by the first enzyme, where the first enzyme is not supported on an electrode used in an electrochemical method.

6. Sensor of the Present Application

Furthermore, as a sixth aspect of the present application, there is provided a sensor which measures the analyte, which comprises electrodes including a working electrode and a counter electrode, where a first enzyme and the catalase inhibitor of the present application are supported to the electrode. The electrode may further support a second enzyme. The examples of the first enzyme and the second enzyme are as described above. The constituent materials of the electrodes are not specifically limited and may be any material usually used for electrochemical quantification of the hydrogen peroxide, such as platinum, gold, silver, palladium, carbon, iridium, and iridium oxide. The platinum or the palladium is preferably used as the electrode material. The sensor may further contain a reference electrode. The method for supporting the enzyme and the catalase inhibitor on the electrode may be any method as long as the desired enzyme and the catalase inhibitor can be supported on the electrodes and is not specifically limited. Any of methods known in the art can be used. For example, the inkjet method may be used.

For example, when HbA1c is used as an analyte, an HbA1c sensor where the fructosyl peptide oxidase or a fructosyl amino-acid oxidase instead of the fructosyl peptide oxidase and the catalase inhibitor of the present application are supported on an electrodes is provided. In the HbA1c sensor, a protease may be supported on the electrode.

The following describes the present application in detail based on working examples, however these working examples do not limit the present invention by any means.

Example 1

Catalase Inhibitory Effect Test (Foaming Test)
(Method)

2-azido-1,3-dimethylimidazolinium hexafluorophosphate (0.001% (w/v)) or sodium azide (0.001% (w/v)), and protease (actinase E, 18000 U/mL), anionic surfactant (sodium N-dodecanoylsarcosinate 0.5% (w/v)), potassium glutamate (300 mM), bis-tris buffer solution (10 mM, pH 6.5), and human blood (equivalent to dilution by 25 times) were mixed. After an elapse of four minutes and 30 seconds after the addition of the blood, hydrogen peroxide 1% (v/v) was introduced in the mixed liquid. Whether foaming (oxygen production) occurred or not after the introduction of the hydrogen peroxide was confirmed by visual check. The concentrations of the respective constituents indicate their final concentrations at the end of the reaction.
(Results)

The foam was not observed after the introduction of the hydrogen peroxide in the case of adding any of 2-azido-1,3-dimethylimidazolinium hexafluorophosphate or the sodium azide. This suggests that the catalase in the blood could be suppressed.

Example 2

Electrochemical Measurement Test of HbA1c Using Catalase Inhibitor (1)
(Method)

Protease (actinase E, 2250 U/mL), anionic surfactant (sodium N-dodecanoylsarcosinate 5.0% (w/v)), potassium glutamate (300 mM), potassium phosphate buffer solution (30 mM, pH 8), a catalase inhibitor, and the certified reference material for measurement of HbA1c (obtained from Reference Material Institute for Clinical Chemistry Standards, the materials equivalent to dilution by 25 times of respective level 1, level 3, and level 5 of JCCRM 411 were used) were mixed to prepare a solution for measurement. Sodium azide (350 μM or 1750 μM) or 2-azido-1,3-dimethylimidazolinium hexafluorophosphate (350 μM or 1750 μM) was used as the catalase inhibitor.

Fructosyl peptide oxidase (229 U/ml), carboxymethyl cellulose (0.125% (w/v)), potassium phosphate buffer solution (25 mM, pH 8), potassium glutamate (10 mM), and trehalose (0.5% (w/v)) were supported to a sensor including a working electrode and a counter electrode formed of palladium electrodes.

The solution for measurement was spotted on the sensor, 0.62 V was applied between the working electrode and the counter electrode for one second, and 0.25 V was applied to the working electrode and the counter electrode after standing still for 15 seconds, and then a current value after ten seconds was measured.

The concentrations of the respective constituents indicate their final concentrations in the solution for measurement.
(Results)

Figure 1:
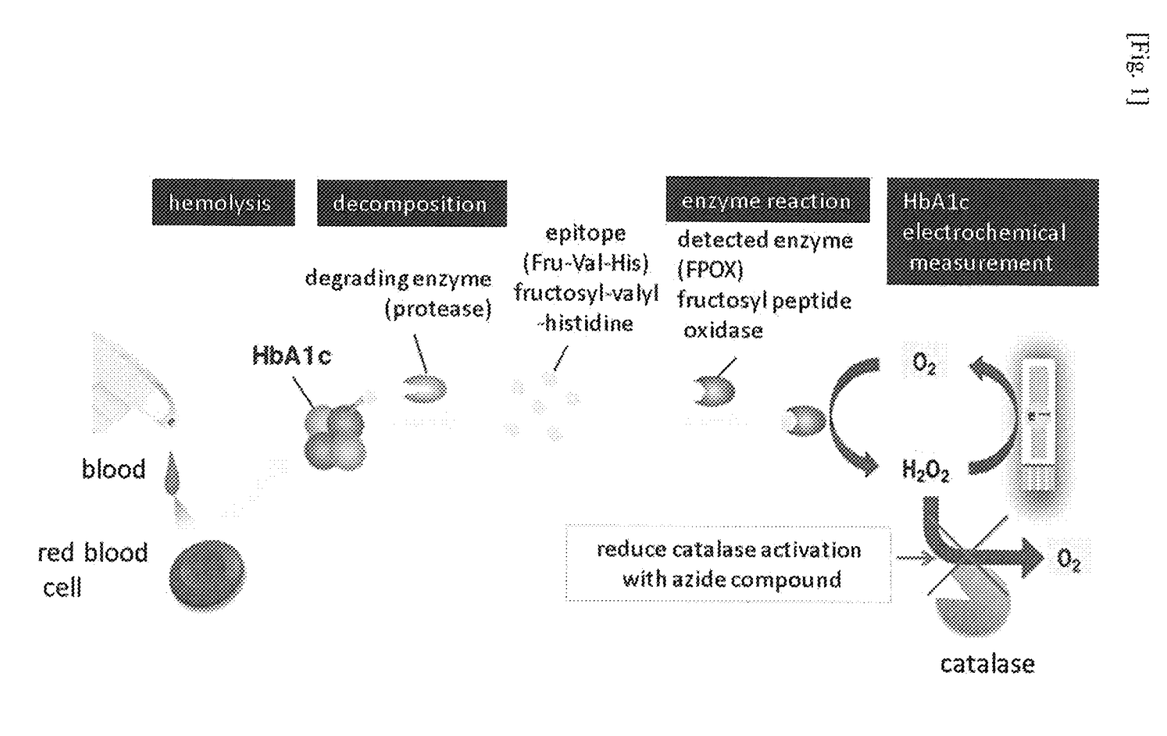
FIG. 1 is a schematic diagram illustrating one example of a method for measuring an analyte using a catalase inhibitor of the present application.
Figure 2:
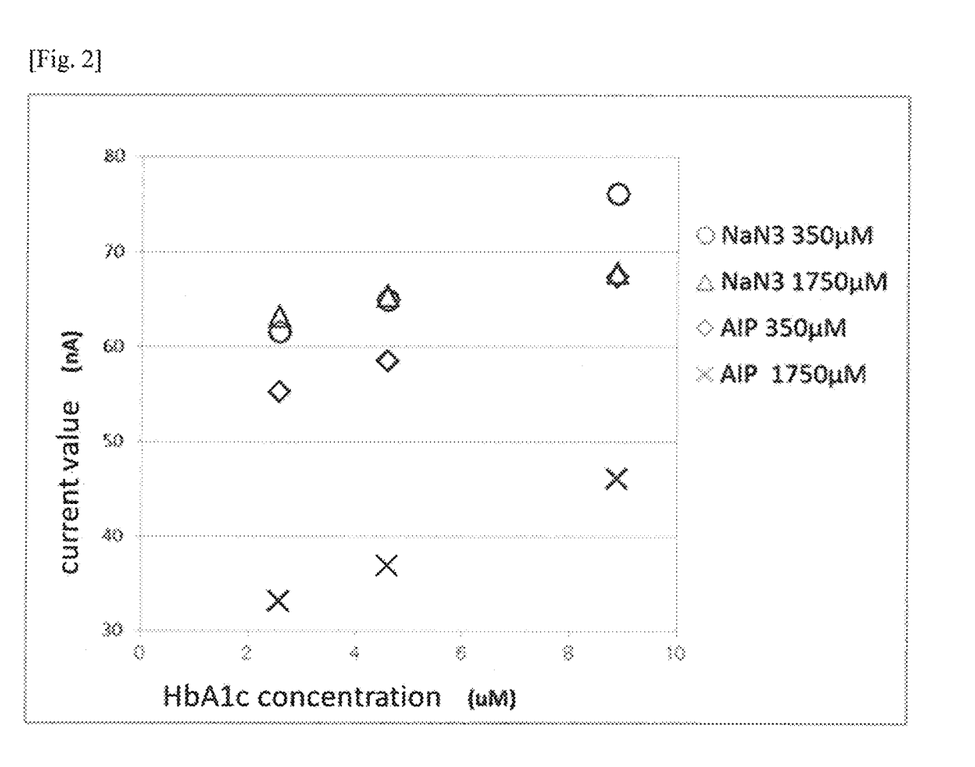
FIG. 2 illustrates a current response to an HbA1c concentration when sodium azide or 2-azido-1,3-dimethylimidazolinium hexafluorophosphate was each added by 350 μM and 1750 μM. In the drawing, "NaN3" indicates sodium azide and "AIP" indicates 2-azido-1,3-dimethylimidazolinium hexafluorophosphate.

FIG. 2 illustrates the results. FIG. 2 illustrates a current response to HbA1c concentration when sodium azide or 2-azido-1,3-dimethylimidazolinium hexafluorophosphate was each added by 350 μM or 1750 μM. Table 1 shows formulae of linear approximation curves of the respective measurement results, and Table 2 shows values obtained by dividing gradients of the linear approximation curves by intercepts.

In the tables, "$NaN_3$" indicates the sodium azide, and "AIP" indicates the 2-azido-1,3-dimethylimidazolinium hexafluorophosphate.

TABLE 1

|  | Linear Approximation Curve |
|---|---|
| $NaN_3$ 350 μM | y = 2.35x + 54.99 |
| $NaN_3$ 1750 μM | y = 0.69x + 61.74 |
| AIP 350 μM | y = 1.95x + 49.97 |
| AIP 1750 μM | y = 2.06x + 27.71 |

TABLE 2

|  | Sensitivity (Gradient of Approximated Curve ÷ Intercept) |
|---|---|
| $NaN_3$ 350 μM | 0.043 |
| $NaN_3$ 1750 μM | 0.011 |
| AIP 350 μM | 0.039 |
| AIP 1750 μM | 0.074 |

As apparent from FIG. 2 and Tables 1 and 2, there were no large differences in the gradients of the approximated curves and the sensitivity (S/N ratio) between sodium azide and 2-azido-1,3-dimethylimidazolinium hexafluorophosphate at 350 μM; however, the gradient of the approximated curve of sodium azide largely lowered at 1750 μM and the sensitivity lowered. On the other hand, a decrease in the gradient of the approximated curve of 2-azido-1,3-dimethylimidazolinium hexafluorophosphate was not observed at 1750 μM, and further the value of the intercept decreased; therefore, an improvement in sensitivity (S/N ratio) was observed. Accordingly, it has been found that the electrical sensitivity of the hydrogen peroxide was improved, thereby the measurement accuracy was enhanced when 2-azido-1,3-dimethylimidazolinium hexafluorophosphate was used as the catalase inhibitor.

Example 3

Electrochemical Measurement Test of HbA1c Using Catalase Inhibitor (2)
(Method)

The current value relative to the HbA1c concentration was measured by the method identical to that of Example 2. However, as the catalase inhibitor, 2-azido-1,3-dimethylimidazolinium hexafluorophosphate (1750 μM or 3500 μM) was used.
(Results)

Figure 3:
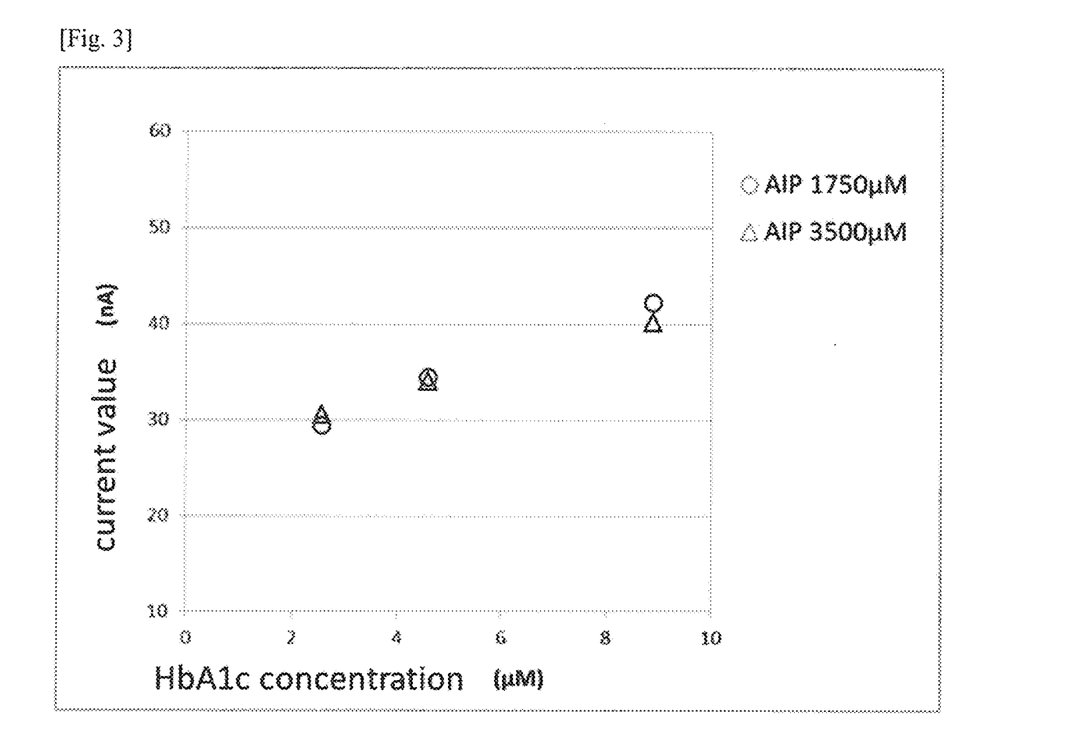
FIG. 3 illustrates a current response to the HbA1c concentration when 2-azido-1,3-dimethylimidazolinium hexafluorophosphate was added by 1750 μM or 3500 μM. In the drawing, "AIP" indicates 2-azido-1,3-dimethylimidazolinium hexafluorophosphate.

FIG. 3 illustrates the results. FIG. 3 illustrates a current response to HbA1c concentration when 1750 μM or 3500 μM 2-azido-1,3-dimethylimidazolinium hexafluorophosphate was added. Table 3 shows formulae of linear approximation curves of the respective measurement results, and Table 4 shows values obtained by dividing gradients of the linear approximation curves by intercepts.

In the tables, "AIP" indicates the 2-azido-1,3-dimethylimidazolinium hexafluorophosphate.

TABLE 3

| | Linear Approximation Curve |
|---|---|
| AIP 1750 μM | y = 1.99x + 24.78 |
| AIP 3500 μM | y = 1.50x + 26.93 |

TABLE 4

| | Sensitivity (Gradient of Approximated Curve ÷ Intercept) |
|---|---|
| AIP 1750 μM | 0.080 |
| AIP 3500 μM | 0.056 |

As apparent from FIG. 3 and Tables 3 and 4, it has been found that sufficient measurement sensitivity was obtained also when 3500 μM 2-azido-1,3-dimethylimidazolinium hexafluorophosphate was used.

Example 4

Figure 4:
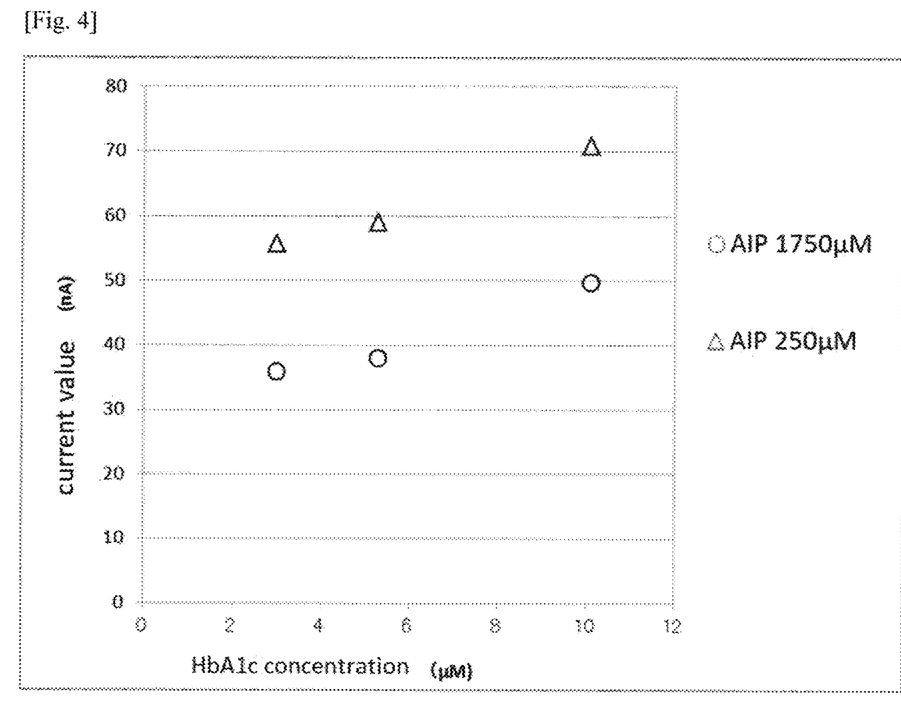
FIG. 4 illustrates a current response to the HbA1c concentration when 2-azido-1,3-dimethylimidazolinium hexafluorophosphate was added by 1750 μM or 250 μM. In the drawing, "AIP" indicates 2-azido-1,3-dimethylimidazolinium hexafluorophosphate.

Electrochemical Measurement Test of HbA1c Using Catalase Inhibitor (3)
(Method)
The current value relative to HbA1c concentration was measured by the method identical to that of Example 2. However, as the catalase inhibitor, 2-azido-1,3-dimethylimidazolinium hexafluorophosphate (1750 μM or 250 μM) was used.
(Results)
FIG. 4 illustrates the results. FIG. 4 illustrates a current response to HbA1c concentration when 1750 μM or 250 μM 2-azido-1,3-dimethylimidazolinium hexafluorophosphate was added. Table 5 shows formulae of linear approximation curves of the respective measurement results, and Table 6 shows values obtained by dividing gradients of the linear approximation curves by intercepts.
In the tables, "AIP" indicates the 2-azido-1,3-dimethylimidazolinium hexafluorophosphate.

TABLE 5

| | Linear Approximation Curve |
|---|---|
| AIP 1750 μM | y = 2.02x + 28.89 |
| AIP 250 μM | y = 2.21x + 48.39 |

TABLE 6

| | Sensitivity (Gradient of Approximated Curve ÷ Intercept) |
|---|---|
| AIP 1750 μM | 0.070 |
| AIP 250 μM | 0.046 |

As apparent from FIG. 4 and Tables 5 and 6, it has been found that sufficient measurement sensitivity was obtained also when 250 μM 2-azido-1,3-dimethylimidazolinium hexafluorophosphate was used.

INDUSTRIAL APPLICABILITY

A catalase inhibitor of the present application can be used for a method for measuring various analytes based on an amount of hydrogen peroxide produced. For example, the catalase inhibitor is also usable for measurement of a blood glucose level.

The invention claimed is:

1. A method for measuring an analyte based on production of hydrogen peroxide, comprising the following steps:
(A) a step of mixing a sample and a catalase inhibitor comprising a compound represented by formula (I):

wherein $R_1$, $R_2$, $R_3$ and $R_4$ each independently represents a hydrogen atom, a halogen, an amino group, a hydroxyl group, a carboxyl group, or a hydrocarbon group having 1 to 4 carbons which may contain substituent(s); and $X^-$ represents an anionic chemical species, wherein the sample comprises the analyte and a catalase;
(B) a step of oxidizing the analyte by a first enzyme to produce hydrogen peroxide; and
(C) a step of measuring the hydrogen peroxide.

2. The method for measuring an analyte according to claim 1, wherein
step (B) is performed after step (A) or simultaneously with step (A).

3. A method for measuring an analyte based on production of a hydrogen peroxide, comprising the following steps:
(a) a step of mixing a sample and a catalase inhibitor comprising a compound represented by formula (I):

wherein $R_1$, $R_2$, $R_3$ and $R_4$ each independently represents a hydrogen atom, a halogen, an amino group, a hydroxyl group, a carboxyl group, or a hydrocarbon group having 1 to 4 carbons which may contain substituent(s); and $X^-$ represents an anionic chemical species, wherein the sample comprises the analyte and a catalase;
(b-1) a step of producing a substrate from the analyte by a second enzyme;
(b-2) a step of oxidizing the substrate by a first enzyme to produce hydrogen peroxide; and
(c) a step of measuring the hydrogen peroxide.

4. The method for measuring an analyte according to claim 3, wherein
the steps are performed:
in an order of (b-1), (a), (b-2), and then (c);
after step (b-1), steps (a) and (b-2) are performed simultaneously, and then step (c) is performed; or
steps (a) and (b-1) are performed simultaneously, and then step (c) is performed after step (b-2).

5. The method for measuring an analyte according to claim 1, wherein in step (C), the hydrogen peroxide is measured by a colorimetry, a chemiluminescence method, or an electrochemical method.

6. A measurement kit which measures an analyte in a sample comprising a catalase, comprising:
a first enzyme which catalyzes a reaction where the analyte is oxidized to produce hydrogen peroxide; and
a catalase inhibitor comprising a compound represented by formula (I):

wherein $R_1$, $R_2$, $R_3$ and $R_4$ each independently represents a hydrogen atom, a halogen, an amino group, a hydroxyl group, a carboxyl group, or a hydrocarbon group having 1 to 4 carbons which may contain substituent(s); and $X^-$ represents an anionic chemical species.

7. A measurement kit that measures an analyte in a sample comprising a catalase, comprising:
a first enzyme which catalyzes a reaction where a substrate is oxidized to produce hydrogen peroxide;
a catalase inhibitor comprising a compound represented by formula (I):

wherein $R_1$, $R_2$, $R_3$ and $R_4$ each independently represents a hydrogen atom, a halogen, an amino group, a hydroxyl group, a carboxyl group, or a hydrocarbon group having 1 to 4 carbons which may contain substituent(s); and $X^-$ represents an anionic chemical species; and
a second enzyme which catalyzes a reaction where the substrate is produced from the analyte.

8. The kit according to claim 6, further comprising a peroxidase.

9. A kit for pretreatment of a sample for measurement of an analyte in the sample comprising a catalase by an electrochemical method, based on production of hydrogen peroxide by oxidization of a substrate by a first enzyme, wherein the kit for pretreatment of the sample comprises:
a catalase inhibitor comprising a compound represented by formula (I):

wherein $R_1$, $R_2$, $R_3$ and $R_4$ each independently represents a hydrogen atom, a halogen, an amino group, a hydroxyl group, a carboxyl group, or a hydrocarbon group having 1 to 4 carbons which may contain substituent(s); and $X^-$ represents an anionic chemical species; and
a second enzyme which catalyzes a reaction where the substrate is produced from the analyte.

10. The method according to claim 1, wherein
$R_1$, $R_2$, $R_3$ and $R_4$ each independently represents a hydrogen atom or a hydrocarbon group having 1 to 4 carbons, wherein the hydrocarbon group may contain at least one kind of substituent selected from the group consisting of a halogen, an amino group, a hydroxyl group, and a carboxyl group; and
$X^-$ represents any one selected from the group consisting of a halogen ion, an ion in a compound containing halogen(s), a hydroxide ion, a carboxylate ion, a nitrate ion, a nitrite ion, an acetate ion, a carbonic acid hydrogen ion, a dihydrogen phosphate ion, a hydrogen sulfate ion, a hydrogen sulfide ion, a hydrogen oxalate ion, a cyanate ion, and a thiocyanate ion.

11. The method according to claim 1, wherein
$R_1$, $R_2$, $R_3$ and $R_4$ each independently represents a hydrogen atom or an unsubstituted, straight-chained or branched-chained saturated hydrocarbon group having 1 to 4 carbons; and
$X^-$ represents a halogen ion or an ion in a compound containing halogen(s).

12. The method according to claim 1, wherein the compound represented by formula (I) is 2-azido-1,3-dimethyl-imidazolinium hexafluorophosphate.

* * * * *